US011152085B2

(12) United States Patent
Doherty et al.

(10) Patent No.: US 11,152,085 B2
(45) Date of Patent: Oct. 19, 2021

(54) USING SENSORS AND LOCATION TO TRIGGER EVENTS AND SHARE DATA

(71) Applicant: International Business Machines Corporation, Armonk, NY (US)

(72) Inventors: Jessica P. Doherty, Poughkeepsie, NY (US); Heidi Lagares-Greenblatt, Jefferson Hills, PA (US); Justin A. McCoy, Austin, TX (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 739 days.

(21) Appl. No.: 15/193,734

(22) Filed: Jun. 27, 2016

(65) Prior Publication Data

US 2017/0372010 A1 Dec. 28, 2017

(51) Int. Cl.
*G16H 10/60* (2018.01)
*G16H 40/67* (2018.01)
*G16H 10/65* (2018.01)

(52) U.S. Cl.
CPC ........... *G16H 10/60* (2018.01); *G16H 10/65* (2018.01); *G16H 40/67* (2018.01)

(58) Field of Classification Search
CPC ..... A61B 5/0022; A61B 5/00252; A61B 5/01; G06Q 50/22–24; G16H 10/60; G16H 40/67; G16H 10/65

(Continued)

(56) References Cited

U.S. PATENT DOCUMENTS 6,024,699 A * 2/2000 Surwit .................. G16H 40/63
600/300
6,374,243 B1 * 4/2002 Kobayashi ............ G06F 16/256
707/703

(Continued)

FOREIGN PATENT DOCUMENTS

CA 2955625 A1 * 2/2016 ............. G06F 1/163

OTHER PUBLICATIONS

Patel et al., "A review of wearable sensors and systems with application in rehabilitation." Journal of Neuroengineering and Rehabilitation, vol. 9 21, Apr. 20, 2012, doi:10.1186/1743-0003-9-21 (Year: 2012).*

(Continued)

*Primary Examiner* — Joy Chng
(74) *Attorney, Agent, or Firm* — Cantor Colburn LLP; Teddi Maranzano (57) ABSTRACT

Embodiments include a system for providing access to secured data; the system includes a processor configured to perform a method. The method includes receiving physiological data from one or more sensors on a wearable device; obtaining environmental data from the one or more sensors; storing the physiological data and the environmental data from the one or more sensors onto a secured storage device; receiving, by a transceiver, a request to access the physiological data; accessing, by a processor, a security profile for the physiological data, wherein the security profile defines a normal range for the physiological data and defines environmental data compliance; and providing access to the physiological data based upon a determination that the physiological data is outside the normal range for the physiological data and based upon a determination that the environmental data is in compliance with the security profile.

18 Claims, 7 Drawing Sheets

(58) Field of Classification Search
USPC .......................................................... 705/2–3
See application file for complete search history.

(56) References Cited

U.S. PATENT DOCUMENTS

| | | | | |
|---|---|---|---|---|
| 6,487,662 | B1* | 11/2002 | Kharon | G06K 9/00006 |
| | | | | 713/186 |
| 7,315,825 | B2* | 1/2008 | Rosenfeld | G16H 40/67 |
| | | | | 705/2 |
| 7,912,733 | B2* | 3/2011 | Clements | G16H 10/60 |
| | | | | 705/2 |
| 8,000,726 | B2* | 8/2011 | Altman | G06Q 30/0259 |
| | | | | 455/456.3 |
| 8,475,367 | B1* | 7/2013 | Yuen | A61B 5/02007 |
| | | | | 600/300 |
| 8,725,462 | B2* | 5/2014 | Jain | G16H 40/67 |
| | | | | 702/187 |
| 9,418,205 | B2* | 8/2016 | Giobbi | G06F 19/00 |
| 9,898,513 | B2* | 2/2018 | McGregor | G06F 16/2477 |
| 2002/0169584 | A1 | 11/2002 | Fu et al. | |
| 2006/0009190 | A1* | 1/2006 | Laliberte | H04W 76/50 |
| | | | | 455/404.1 |
| 2009/0099862 | A1* | 4/2009 | Fireman | G06Q 10/06375 |
| | | | | 705/2 |
| 2009/0322513 | A1 | 12/2009 | Hwang et al. | |
| 2013/0054512 | A1* | 2/2013 | Ephrat | G16H 40/67 |
| | | | | 707/602 |
| 2014/0155705 | A1 | 6/2014 | Papadopoulos et al. | |
| 2014/0337621 | A1* | 11/2014 | Nakhimov | H04W 12/068 |
| | | | | 713/168 |
| 2015/0120572 | A1* | 4/2015 | Slade | G06Q 20/3224 |
| | | | | 705/73 |
| 2015/0305690 | A1 | 10/2015 | Tan et al. | |
| 2015/0351698 | A1 | 12/2015 | Cronin | |
| 2016/0014129 | A1 | 1/2016 | Park et al. | |
| 2016/0042483 | A1* | 2/2016 | Vo | G16H 10/60 |
| | | | | 705/3 |
| 2016/0150362 | A1* | 5/2016 | Shaprio | H04W 4/023 |
| | | | | 340/539.13 |

OTHER PUBLICATIONS

Soh et al., "Wearable Wireless Health Monitoring: Current Developments, Challenges, and Future Trends." IEEE Microwave Magazine, vol. 16, issue 4, pp. 55-70, May 2015, doi: 10.1109/MMM.2015.2394021 (Year: 2015).*

Abo-Zahhad et al., "A Wireless Emergency Telemedicine System for Patients Monitoring and Diagnosis," International Journal of Telemedicine and Applications, vol. 2014 (2014), Article ID 380787, 9 pages.

Y.J. Lin, M.J. Su, S.J. Chen, S.C. Wang, C.I. Lin, H.S. Chen. "A study of ubiquitous monitor with RFID in an elderly nursing home", Proc. on International Conference Multimedia and Ubiquitous Engineering, pp. 336-340, 2007.

* cited by examiner

USING SENSORS AND LOCATION TO TRIGGER EVENTS AND SHARE DATA

BACKGROUND

The present disclosure relates to data sharing, and more specifically, to using sensors and location to trigger events and share data.

Wearable sensors and devices are allowing people to continuously monitor various aspects of their day to day lives including monitoring physiological data about the wearer. As technology advances, additional healthcare applications will be developed allowing a wearer to have more accessible data about their physiological conditions.

Finding health issues or abnormal changes in a person's vitals in a timely manner is important for many situations. For example, if a person is unconscious or not responsive, there is a possibility that the medical staff does not know what has happened to the person or the medical history of the person. For these types of situations, medical staff or even family members may not be able to reach data from the person's wearable devices due to a lack of clarity on privacy or interoperability of the device.

SUMMARY

Embodiments include a computer system for providing access to secured data, the computer system including a server having a processor, the processor configured to perform a method. The method includes receiving physiological data from one or more sensors on a wearable device; obtaining environmental data from the one or more sensors; storing the physiological data and the environmental data from the one or more sensors on to a secured storage device; receiving, by a transceiver, a request to access the physiological data; accessing, by a processor, a security profile for the physiological data, wherein the security profile defines a normal range for the physiological data and defines environmental data compliance; and providing access to the physiological data based upon a determination that the physiological data is outside the normal range for the physiological data and based upon a determination that the environmental data is in compliance with the security profile.

Embodiments also include a computer program product for providing access to secured data, the computer program product including a non-transitory computer readable storage medium having computer readable program code embodied therewith. The computer readable program code including computer readable program code configured to perform a method. The method includes receiving physiological data from one or more sensors on a wearable device; obtaining environmental data from the one or more sensors; storing the physiological data and the environmental data from the one or more sensors on to a secured storage device; receiving, by a transceiver, a request to access the physiological data; accessing, by a processor, a security profile for the physiological data, wherein the security profile defines a normal range for the physiological data and defines environmental data compliance; and providing access to the physiological data based upon a determination that the physiological data is outside the normal range for the physiological data and based upon a determination that the environmental data is in compliance with the security profile.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

In accordance with exemplary embodiments of the disclosure, methods, systems and computer program products for providing access to secured data are provided. In exemplary embodiments, methods, systems, and computer program products for providing access to secured data includes a user wearable device configured to receive and store sensor readings from one or more sensors. These sensor readings include physiological data about a user as well as environmental conditions surrounding the user. This physiological data and environmental data are stored in a secured storage device either within the user wearable device or in a cloud environment. A security profile is present which determines when and if this physiological data can be shared with third parties. The security profile includes a normal range of the physiological data and when this physiological data is outside of this normal range, it can unlock the physiological data for access by a third party according to a user's preferences.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
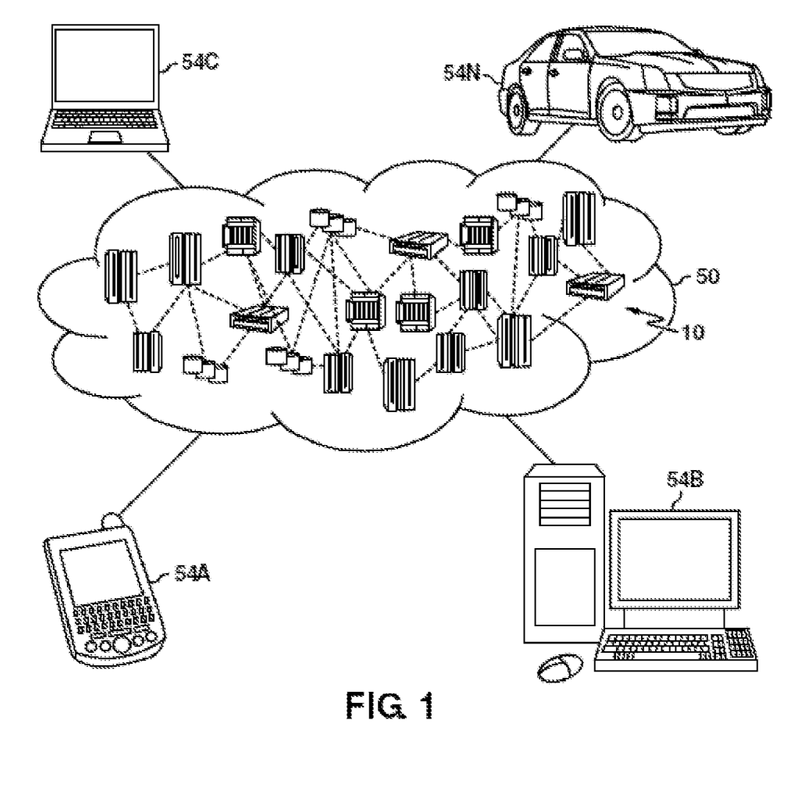
FIG. 1 depicts a cloud computing environment according to one or more embodiments of the present invention.

Referring now to FIG. 1, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
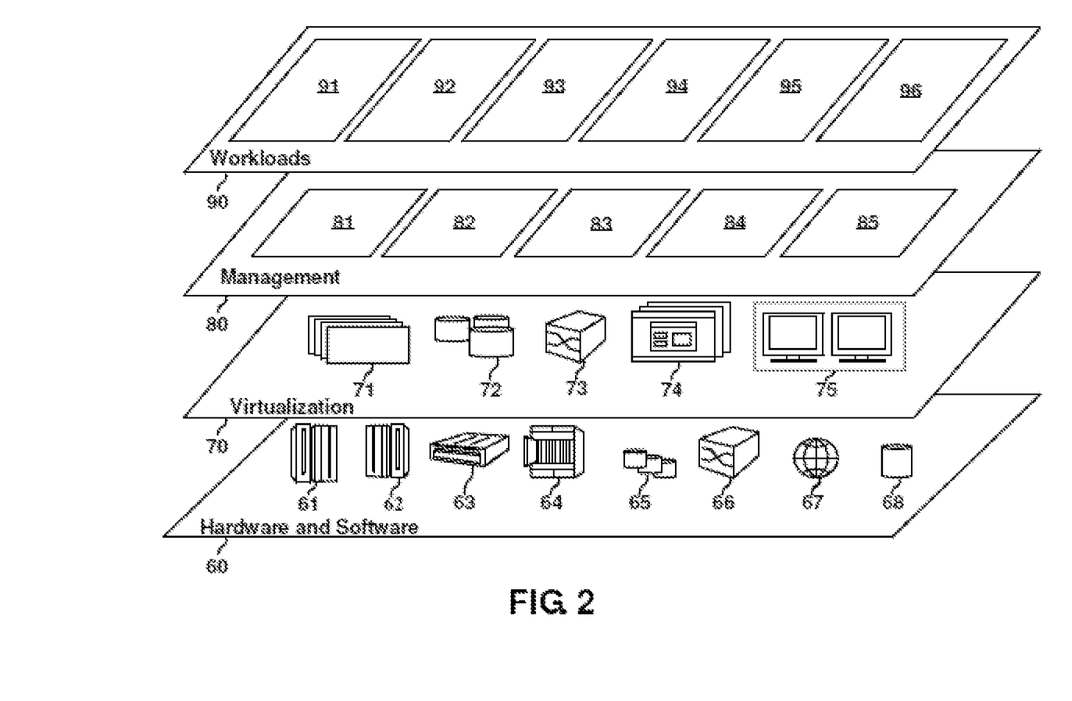
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and providing access to secured data 96.

Figure 3:
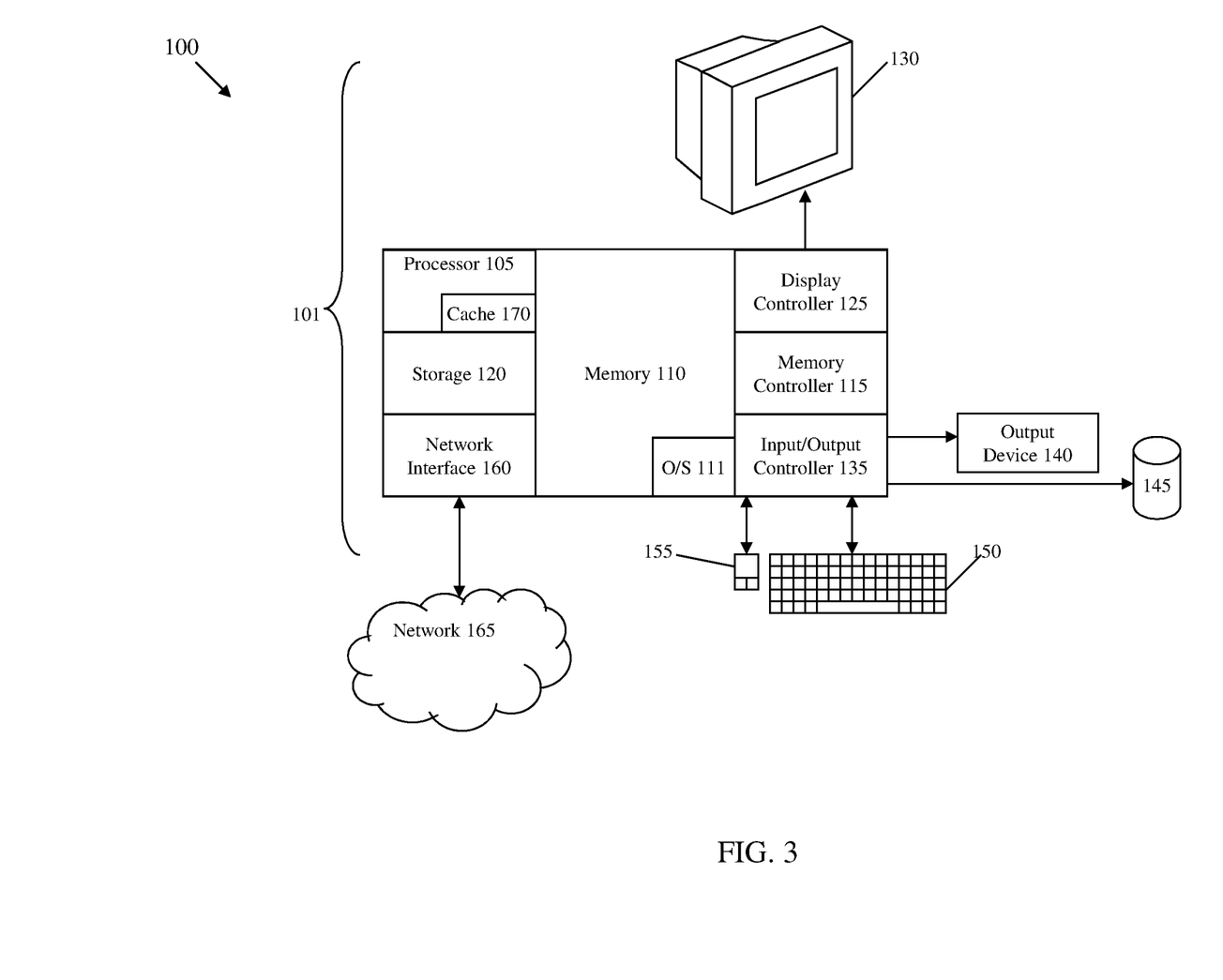
FIG. 3 illustrates a block diagram of a computer system for use in practicing the teachings herein.

FIG. 3 illustrates a block diagram of an exemplary computer system 100 for use with the teachings herein. The methods described herein can be implemented in hardware software (e.g., firmware), or a combination thereof. In an exemplary embodiment, the methods described herein are implemented in hardware and is part of the microprocessor of a special or general-purpose digital computers, such as a personal computer, workstation, minicomputer, or mainframe computer. The system 100, therefore, includes general-purpose computer 101.

In an exemplary embodiment, in terms of hardware architecture, as shown in FIG. 3, the computer 101 includes a processor 105, memory 110 coupled via a memory controller 115, a storage device 120, and one or more input and/or output (I/O) devices 140, 145 (or peripherals) that are communicatively coupled via a local input/output controller 135. The input/output controller 135 can be, for example, but not limited to, one or more buses or other wired or wireless connections, as is known in the art. The input/output controller 135 may have additional elements, which are omitted for simplicity, such as controllers, buffers (caches), drivers, repeaters, and receivers, to enable communications. Further, the local interface may include address, control, and/or data connections to enable appropriate communications among the aforementioned components. The storage device 120 may include one or more hard disk drives (HDD), solid state drives (SSD), or any other suitable form of storage.

The processor 105 is a computing device for executing hardware instructions or software, particularly that stored in memory 110. The processor 105 can be any custom made or commercially available processor, a central processing unit (CPU), an auxiliary processor among several processors associated with the computer 101, a semiconductor based microprocessor (in the form of a microchip or chip set), a macroprocessor, or generally any device for executing instructions. The processor 105 may include a cache 170, which may be organized as a hierarchy of more cache levels (L1, L2, etc.).

The memory 110 can include any one or combination of volatile memory elements (e.g., random access memory (RAM, such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 110 may incorporate electronic, magnetic, optical, and/or other types of storage media. Note that the memory 110 can have a distributed architecture, where various components are situated remote from one another, but can be accessed by the processor 105.

The instructions in memory 110 may include one or more separate programs, each of which comprises an ordered listing of executable instructions for implementing logical functions. In the example of FIG. 3, the instructions in the memory 110 include a suitable operating system (OS) 111. The operating system 111 essentially controls the execution of other computer programs and provides scheduling, input-output control, file and data management, memory management, and communication control and related services.

In an exemplary embodiment, a conventional keyboard 150 and mouse 155 can be coupled to the input/output controller 135. Other output devices such as the I/O devices 140, 145 may include input devices, for example, but not limited to a printer, a scanner, microphone, and the like.

Finally, the I/O devices 140, 145 may further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The system 100 can further include a display controller 125 coupled to a display 130. In an exemplary embodiment, the system 100 can further include a network interface 160 for coupling to a network 165. The network 165 can be an IP-based network for communication between the computer 101 and any external server, client and the like via a broadband connection. The network 165 transmits and receives data between the computer 101 and external systems. In an exemplary embodiment, network 165 can be a managed IP network administered by a service provider. The network 165 may be implemented in a wireless fashion, e.g., using wireless protocols and technologies, such as Wi-Fi, WiMax, etc. The network 165 can also be a packet-switched network such as a local area network, wide area network, metropolitan area network, Internet network, or other similar type of network environment. The network 165 may be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 101 is a PC, workstation, intelligent device or the like, the instructions in the memory 110 may further include a basic input output system (BIOS) (omitted for simplicity). The BIOS is a set of essential routines that initialize and test hardware at startup, start the OS 111, and support the transfer of data among the storage devices. The BIOS is stored in ROM so that the BIOS can be executed when the computer 101 is activated.

When the computer 101 is in operation, the processor 105 is configured to execute instructions stored within the memory 110, to communicate data to and from the memory 110, and to generally control operations of the computer 101 pursuant to the instructions.

Figure 4:
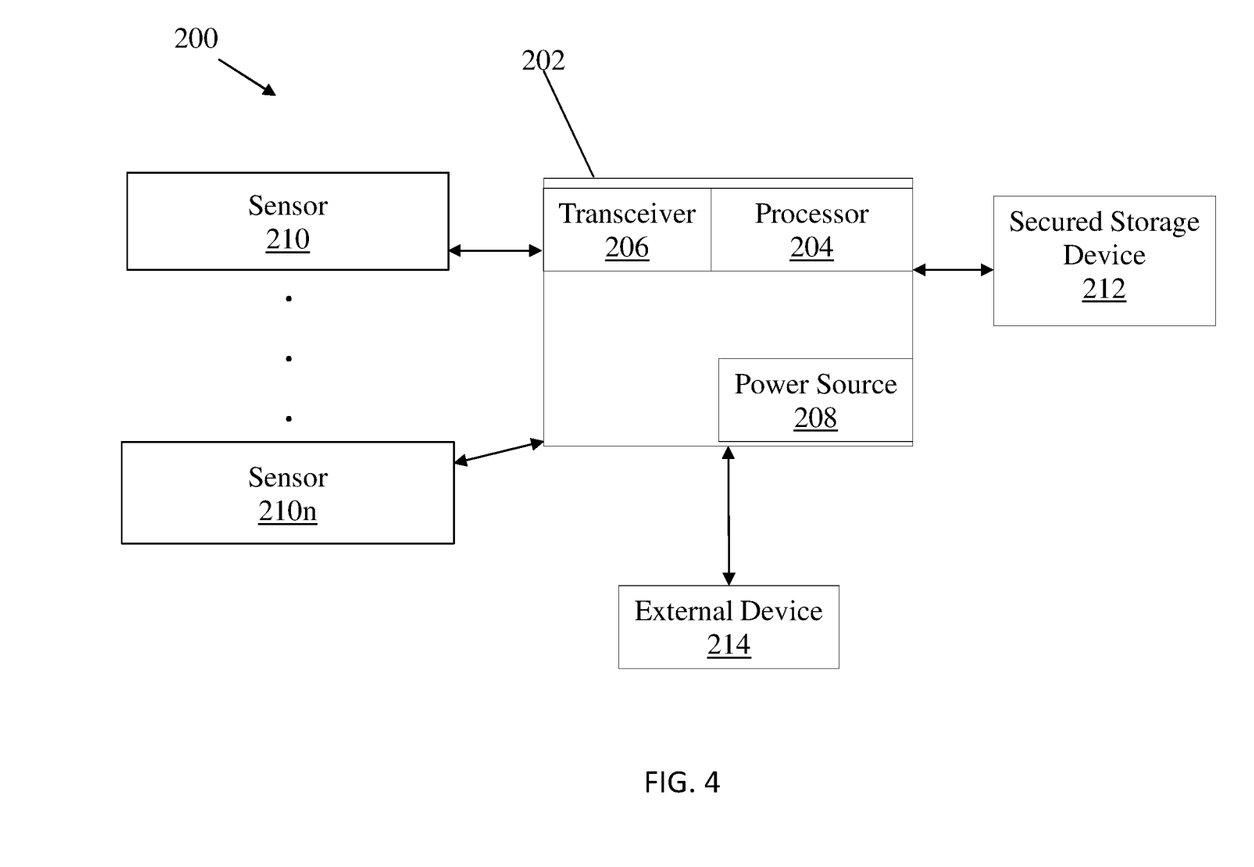
FIG. 4 illustrates a block diagram of a system for providing access to secured data in accordance with an embodiment.

FIG. 4 illustrates a system 200 for providing access to secured data according to an exemplary embodiment. In one or more embodiments, the system includes a user wearable device 202, one or more sensors 210 . . . 210n, a secured storage 212, and an external device 214. The user wearable device 202 includes a processor 204, a transceiver 206, and a power source 208.

In one or more embodiments, the user wearable device 202 can include any of a smartwatch, fitness tracking device, medical sensor, and any other wearable user device. The wearable user device 202 is communicatively coupled to the one or more sensors 210 . . . 210n. One of skill in the art can appreciate these one or more sensors 210 . . . 210n can be in wired communication or wireless communication with the user wearable device 202. In addition, the one or more sensors 210 . . . 210n can be entirely or partially contained within the user wearable device 202 or a separate sensor device. In one or more embodiments, the one or more sensors 210 . . . 210n are configured to measure physiological data such as heart rate, blood sugar, blood pressure, pulse, blood oxygenation levels and the like. In addition, the one or more sensors 210 . . . 210n may include environmental sensors that are configured to measure environmental data such as but not limited to global positioning system (GPS) location data, velocity, temperature, and humidity.

In one or more embodiments, the system 200 includes a secured storage device 212. The secured storage device 212 can be entirely contained within the user wearable device 202 or it can be stored on a computing device that is communicatively coupled to the user wearable device 202. The secured storage device 212 can reside on a server in a cloud computing environment. For example, the user wearable device 202 may receive physiological data from the one or more sensors 210 . . . 210n and may transmit this physiological data, via the transceiver 206, to a cloud computing environment for secure storage and remote access. In addition to physiological data stored on the secured storage device, a user may store other information such as, for example, historical medical data (i.e. diagnosis information, current medication, immunization history, etc.), user information (i.e., name, address, emergency contact), and medical insurance information. This other information can be inputted into the secured storage device by the user or information such as medical history may be taken from historical physiological data. In one or more embodiment, the other information can include information stored in the device such as historical GPS location data, recent photos, previous text messages, phone calls, and emails and the like.

In one or more embodiments, the system 200 includes an external device 214 which can access and request access to the physiological data from the user-wearable device 202. The external device 214 can include external computers or other device configured to communicate with the user wearable device 202 via the transceiver 206 to determine access rights for the physiological data contained on the secure storage device 212.

In one or more embodiments, the user wearable device 202 includes a security profile which sets access rights and conditions for access to the physiological data and other information stored in the secured storage device 212. In addition, the security profile can set what physiological data and other information is available for access. For example, a user can designate that only blood sugar levels may be accessed. Also, the security profile can set restrictions on when blood sugar levels can be accessed. For example, a user may set their security profile to allow access to blood sugar levels when the sensors detect abnormal blood sugar levels such as too low and too high. In one or more embodiments, the system 200 can be employed in a health care emergency. For example, the user wearable device 202 may be a sensing device that is configured to collect blood sugar data for a user. The user may be unconscious and may not be able to communicate to a healthcare professional their present and past condition and may arrive at a hospital. A hospital worker, such as a nurse, doctor, etc., may utilize an external device 214 to request physiological data from the user wearable device 202. The user wearable device contains a security profile which dictates what physiological data and other information may be shared based upon certain conditions being met. In an embodiment, one of the conditions to be met may be that the physiological data is shared if the user's blood sugar is below normal or below a set level by the user. The security profile may allow a hospital worker to view only the blood sugar data or may allow the hospital to view all information contained within the secured storage device 212. In addition, another condition to be met is an environmental condition such as GPS location which is supplied by the sensors 210 . . . 210n. The environmental condition can look at GPS location and recognize that the user device is located at a hospital or other medical facility. If the security profile allows physiological data access when the user device is located within a hospital or medical facility, the physiological data will be provided to the external device 214. The external device 214 may be a computer device that can connect to the user device directly or connect via a network or cloud connection.

In one or more embodiments, the security profile on the user wearable device 202 can set access rights for instances when the sensors 210 . . . 210n retrieve physiological data which is outside a pre-defined threshold level. When the physiological data exceeds or falls below this pre-defined threshold level, the user wearable device 202 can provide access to both physiological data and other information as defined by the user. For example, if a user sets the device to release data when the user's internal temperature exceeds a certain level, the user wearable device 202 can provide access to a portion of the physiological data on the user wearable device 202 such as previous temperature readings or it can release all physiological data contained on the user wearable device 202. In addition, other information can be available to release based upon the sensor readings such as other information which includes insurance information of the user, historical medical data, photos, emails and text messages stored on the device, and any additional information the user wishes to provide access to either from the user wearable device 202 or from a cloud server that is housing the information.

In one or more embodiments, the user wearable device 202 can receive a request from an external device 214 for access to physiological data stored either locally on the user wearable device 202 or externally on a server in a cloud computer environment. Based upon a determination that the external user device 214 request is in compliance with a security profile for the user wearable device 202, the physiological data is provided to the external device. In an embodiment, the physiological data is provided by the external device directly accessing the user wearable device 202 to obtain the physiological data stored locally on the user wearable device 202. In another embodiment, the user wearable device 202 can provide the external device 214 with a link, a code, a key or the like to access the physiological data stored on the secured storage device 212 that is housed on a server in a cloud computing environment.

In one or more embodiments, the one or more sensors 210 . . . 210n are configured to periodically obtain environmental data to check for compliance with a security profile. For example, when access to physiological data is granted based upon the GPS location of the user, a security measure can be invoked when the GPS location changes to a new location that is in violation of the security profile. The security measure can include restricting access to some or all of the physiological data and any other information provided to a requester. The security measure may be in the form of a visual, audio, or haptic signal from the user wearable device 202 which informs the user that the security profile has been violated. The user may then restrict the access or access may be automatically restricted when a violation of the security profile occurs. In one or more embodiments, access to the physiological data can be revoked after a certain period of time passes from when access is initially granted. For example, a user wearable device 202 may provide access to the physiological data for a limited period of time such as a 24 hour period according to the security profile.

In one or more embodiments, the user wearable device 202 contains a display that can be either a touch display or a display manipulated by buttons or external input devices, such as a smartphone or computer. In an embodiment, when an external device 214 is requesting access to the physiological data, a pop-up box can display notifying the user that the external device 214 is requesting access and the user can grant or deny this request by selecting an option from the pop-up. One of skill in the art can appreciate that the pop-up box example can include additional means for displaying a notification to a user via a display and also additional means for granting and denying requests. The user wearable device 202 can also notify a user of a request for access via an audio or haptic signal in which the user can either grant or deny the request by pressing a button, inputting a code or key, tapping a touch screen, or any similar means of indicating a yes or no to the access request including but not limited to voice activation.

In one or more embodiments, the security profile for a user can be set by the user or can be set by the user's physician either by programming the security profile into the user wearable device 202 directly or remotely via a network connection. The one or more sensors 210 . . . 210n take periodic readings of physiological data which is then stored in the secured storage device either in real time or updated or synced periodically by the user or automatically by the user wearable device 202.

In one or more embodiments, the security profile can include one or more identifiers that are a condition for access to physiological data. These identifiers can be identifiers for certain medical professionals as identified by the user to allow access when inputted by the external device 214. In one or more embodiments, an emergency code can be inputted by the external device to gain emergency access to the physiological data in cases of emergency. For example, if a patient is traveling and not in a predefined geographical area and emergency care must be administered. A medical professional may input an emergency code that will override the security profile and allow access to the physiological data. In one or more embodiments, the security profile can identify certain physiological data and other information as available when an emergency code is received. For example, a user can set the security profile to allow access to physiological data related to blood pressure and also complete medical history in a case where an emergency code is utilized.

In one or more embodiments, the security profile can detect a change in physiological data that goes outside the normal range for the physiological data. When this occurs, the user wearable device 202 can then obtain environmental data to determine if the security profile has been violated thus allowing access to the physiological data. For example, if a user's heart rate increases dramatically, the user wearable device 202 would then look to the speed at which the user wearable device 202 is traveling to determine that the user is exercising and running and thus not necessarily unlock the physiological data for access. In another example, a user's blood pressure may be elevated and outside a normal range; however, environmental conditions as detected by the one or more sensors 210 . . . 210n could determine an increase in ambient temperature and would determine that unlocking access to the physiological data is not appropriate at this time. In an embodiment, certain physiological conditions, such as too low blood sugar, may cause unlocking of the physiological data regardless of environmental conditions.

In one or more embodiments, the user wearable device 202 may notify the user of abnormal physiological data through a visual, audio, or haptic (vibrating) signal. The user may then verify if these abnormal readings are caused by increased stress, exercise, temperature and the like and not allow the unlocking of the physiological data.

In one or more embodiments, the security profile can utilize a learning model to adjust to a user's schedule and any changes in physiological data. For example, if a user continues to confirm that the user was running during increase heart rate and blood pressure each morning during the user's morning run, the model will identify this and adjust the conditions for the normal range of heart rate for that period of time.

In one or more embodiments, the user wearable device 202 can be configured to trigger the contacting of an emergency contact should physiological data fall outside a normal range. The emergency contact may be notified via text, email, phone call and the like to indicate there may be an emergency occurring with the user of the user wearable device 202 based upon the physiological data. The emergency contact can be completed in sequence based upon the physiological data over time. For example, if a user's blood sugar levels begin to drop, an emergency text or call can go to a family member to have the family member contact the user to have them eat something. If the blood sugar levels continue to drop and reach dangerous levels, a user's physician or emergency personnel may be notified to check up on the user and possibly administer treatment. The data shared to the emergency contact can include physiological data as well as GPS location data to assist in the provision of emergency services.

In one or more embodiments, if the user's physiological data is at very dangerous levels, a signal could be sent to an emergency services dispatch for an ambulance and also the physiological data could be forwarded to the medical facility that the user will be transported.

In one or more embodiments, the movement of the user over time could be measured by the one or more sensors 210 . . . 210n and taken in conjunction with abnormal or dangerous physiological data could indicate an emergency situation and trigger certain events to occur. For example, elevated blood pressure levels and sensor data determining the user has not moved for a certain period of time would trigger an emergency response.

Figure 5:
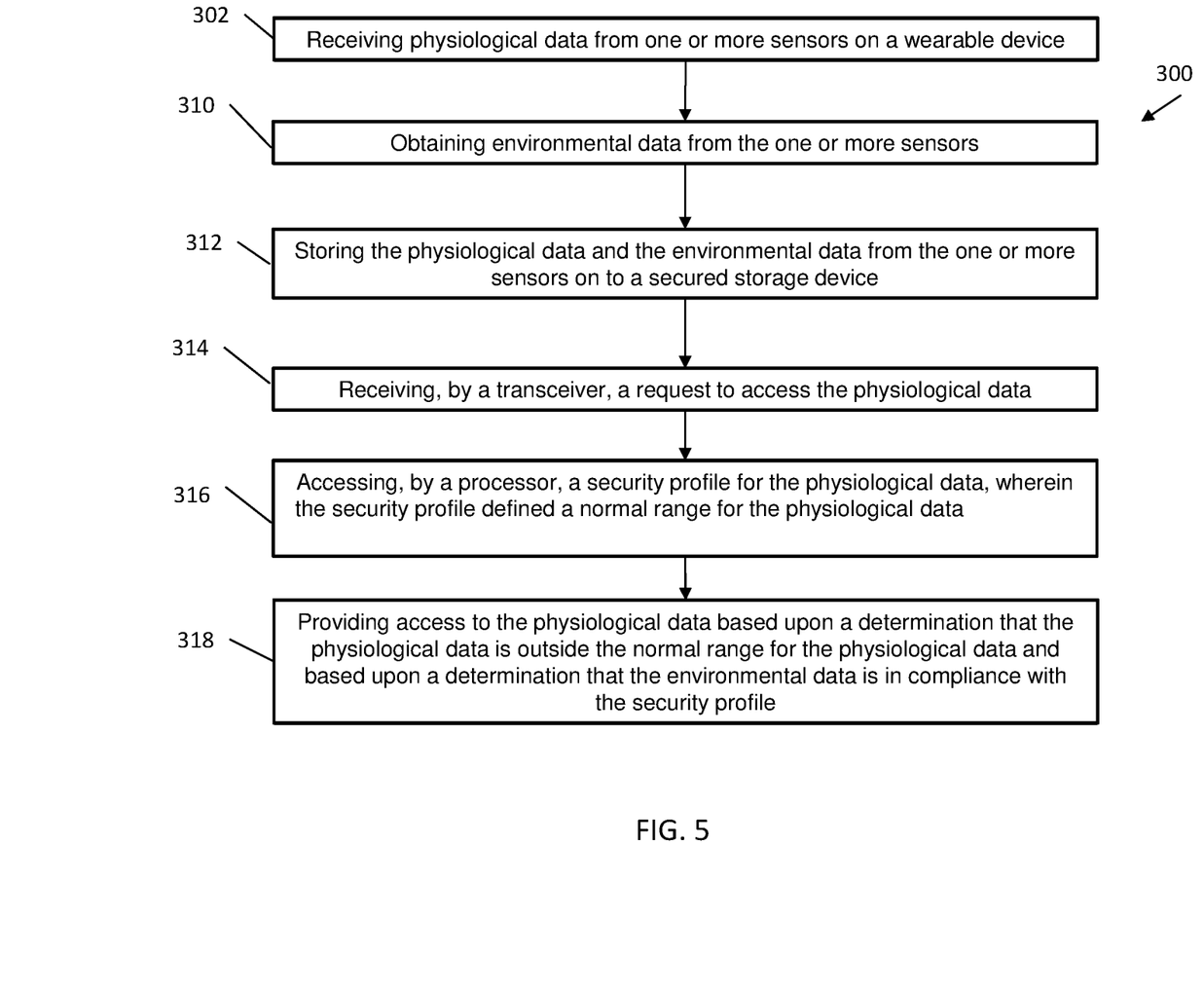
FIG. 5 illustrates a flow diagram of a method for providing access to secured data in accordance with an embodiment.

FIG. 5. Illustrates a flow diagram of a method 300 for providing access to secured data in accordance with one or more embodiments. As shown in block 302, the method 300 includes receiving physiological data from one or more sensors on a wearable device. Next, at block 310, the method includes obtaining environmental data from the one or more sensors. Next, the method 300 includes storing the physiological data from the one or more sensors on a secured storage device, as shown at block 312. Next, the method 300 includes receiving, by a transceiver, a request to access the physiological data, as shown at block 314. Next, at block 316, the method 300 includes accessing, by a processor, a security profile for the physiological data, wherein the security profile defined a normal range for the physiological data and defines environmental data compliance. Next, at block 318, the method 300 includes providing access to the physiological data based upon a determination that the physiological data is outside the normal range for the physiological data and based upon a determination that the environmental data is in compliance with the security profile.

Additional processes may also be included. It should be understood that the processes depicted in FIG. 5 represent illustrations, and that other processes may be added or existing processes may be removed, modified, or rearranged without departing from the scope and spirit of the present disclosure.

Figure 6:
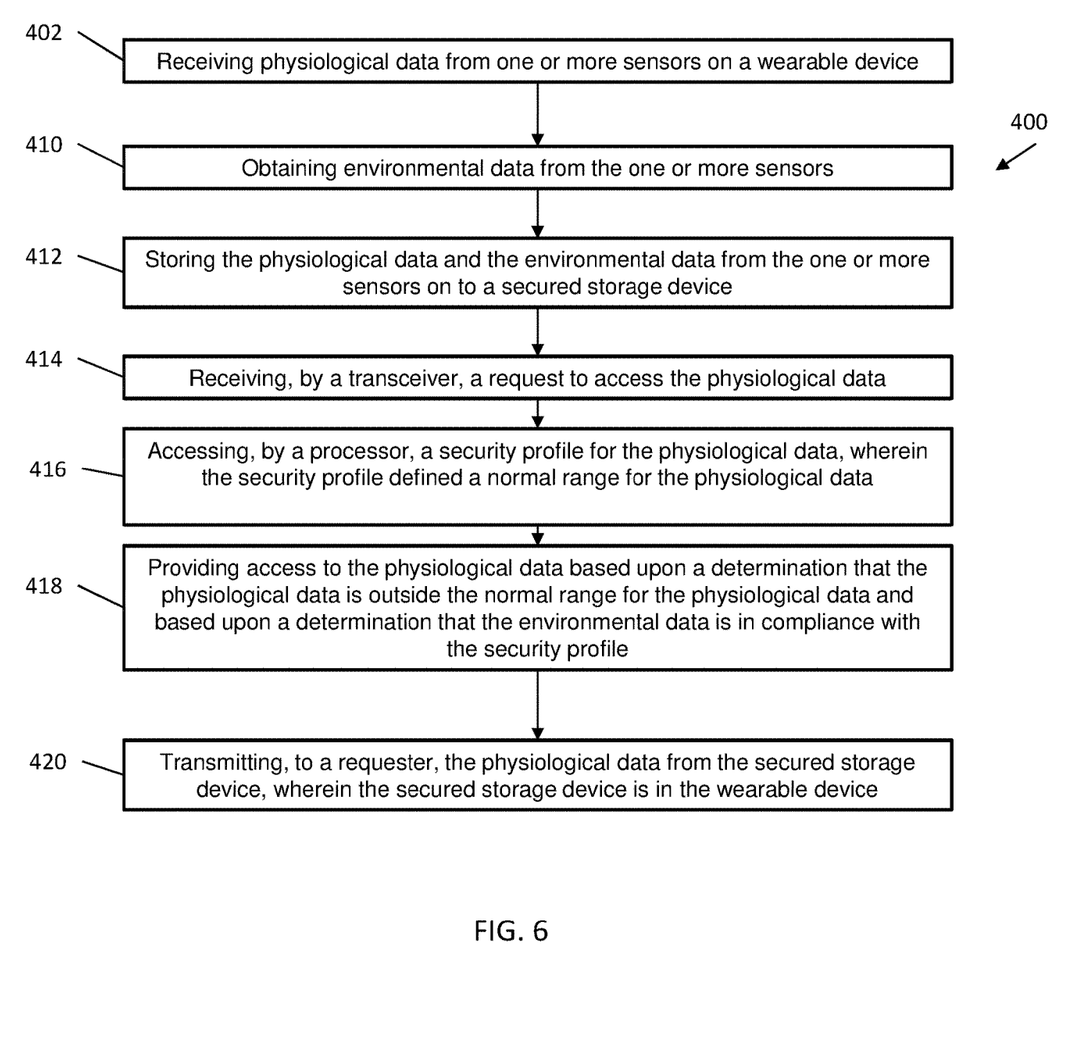
FIG. 6 illustrates a flow diagram of a method for providing access to secured data in accordance with an embodiment.

FIG. 6. Illustrates a flow diagram of a method 400 for providing access to secured data in accordance with one or more embodiments. As shown in block 402, the method 400 includes receiving physiological data from one or more sensors on a wearable device. Next, at block 410, the method includes obtaining environmental data from the one or more sensors. Next, the method 400 includes storing the physiological data from the one or more sensors on a secured storage device, as shown at block 412. Next, the method 400 includes receiving, by a transceiver, a request to access the physiological data, as shown at block 414. Next, at block 416, the method 400 includes accessing, by a processor, a security profile for the physiological data, wherein the security profile defined a normal range for the physiological data and defines environmental data compliance. Next, at block 418, the method 400 includes providing access to the physiological data based upon a determination that the physiological data is outside the normal range for the physiological data and based upon a determination that the environmental data is in compliance with the security profile. Next, at block 420, the method 400 includes transmitting, to a requester, the physiological data from the secured storage device, wherein the secured storage device is in the wearable device.

Additional processes may also be included. It should be understood that the processes depicted in FIG. 6 represent illustrations, and that other processes may be added or existing processes may be removed, modified, or rearranged without departing from the scope and spirit of the present disclosure.

Figure 7:
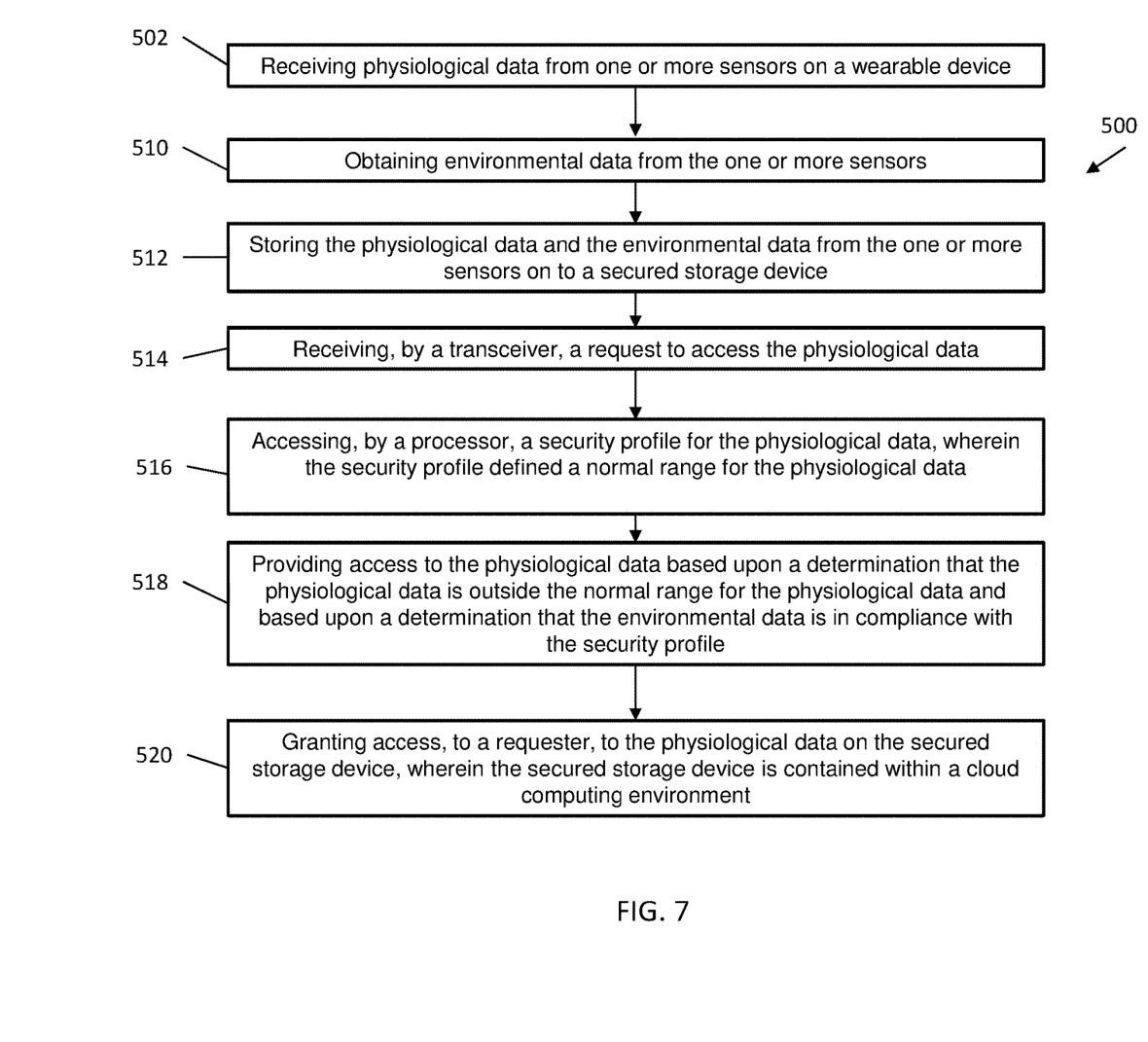
FIG. 7 illustrates a flow diagram of a method for providing access to secured data in accordance with an alternate embodiment.

FIG. 7. Illustrates a flow diagram of a method 500 for providing access to secured data in accordance with one or more embodiments. As shown in block 502, the method 500 includes receiving physiological data from one or more sensors on a wearable device. Next, at block 510, the method includes obtaining environmental data from the one or more sensors. Next, the method 500 includes storing the physiological data from the one or more sensors on a secured storage device, as shown at block 512. Next, the method 500 includes receiving, by a transceiver, a request to access the physiological data, as shown at block 514. Next, at block 516, the method 500 includes accessing, by a processor, a security profile for the physiological data, wherein the security profile defined a normal range for the physiological data and defines environmental data compliance. Next, at block 518, the method 500 includes providing access to the physiological data based upon a determination that the physiological data is outside the normal range for the physiological data and based upon a determination that the environmental data is in compliance with the security profile. Next, at block 520, the method 500 includes granting access, to a requester, to the physiological data on the secured storage device, wherein the secured storage device is contained within a cloud computing environment.

Additional processes may also be included. It should be understood that the processes depicted in FIG. 7 represent illustrations, and that other processes may be added or existing processes may be removed, modified, or rearranged without departing from the scope and spirit of the present disclosure.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting-data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for providing access to secured data, the method comprising:
   receiving, from one or more sensors on a wearable device, physiological data associated with a user of the wearable device;
   obtaining location data from one or more location sensors, wherein the location data comprises global positioning system (GPS) location data of the wearable device;
   storing the physiological data and the location data onto a secured storage device;
   receiving, by a transceiver, a request to access the physiological data;
   accessing, by a processor, a security profile for the physiological data, wherein the security profile defines a normal range associated with the user for the physiological data and defines location data compliance for accessing the physiological data;
   providing access to a portion of the physiological data for a time period based upon a determination that the portion the physiological data is outside the normal range for the physiological data and based upon a determination that the location data is in compliance with the security profile, wherein providing access to the portion physiological data comprises transmitting, to a requester, the physiological data from the secured storage device, wherein the secured storage device is in the wearable device;
   periodically obtaining additional location data from the one or more sensors during the time period, wherein the additional location data comprises additional GPS location data for the wearable device; and
   invoking a security measure for access to the physiological data based upon a determination that the additional location data obtained during the time period is out of compliance with the security profile.

2. The method of claim 1, wherein providing access to the physiological data comprises:
   granting access, to a requester, to the physiological data on the secured storage device, wherein the secured storage device is further contained within a cloud computer environment.

3. The method of claim 2, wherein granting access comprises at least one of sending a link and providing an access code.

4. The method of claim 1, wherein access to the physiological data is provided for a limited period of time.

5. The method of claim 1, wherein access to the physiological data can be revoked by the user.

6. The method of claim 1, wherein the security measure includes at least one of denying access to the physiological data and limiting a scope of access to the physiological data.

7. The method of claim 1, wherein providing access to the physiological data comprises:
   displaying, on the wearable device, indicia showing the request to access the physiological data; and
   receiving an input, from the user, to allow access to the physiological data.

8. The method of claim 1, further comprising:
   denying access to the physiological data based upon a determination that the physiological data is within the normal range for the physiological data.

9. The method of claim 1, further comprising:
   denying access to the physiological data based upon a determination that the environmental data is not in compliance with the security profile.

10. The method of claim 1, wherein the wearable device stores medical data for the user, the medical data comprising historic physiological sensor data about the user of the wearable device, a medication history of the user, or medical insurance information for the user.

11. The method of claim 1, wherein the security profile is created by the user of the wearable device.

12. The method of claim 1, further comprising:
    receiving an emergency code, wherein the emergency code overrides the security profile; and
    providing access to the physiological data.

13. The method of claim 12, further comprising:
    comparing the emergency code to the environmental data; and
    providing access to the secured data based upon a determination that the emergency code corresponds to the environmental data.

14. The method of claim 1, further comprising:
responsive to the physiological data being outside the normal range, accessing contextual data associated with the user from the wearable device; and
blocking access to the physiological data based on a determination that the contextual data justifies the physiological data being outside the normal range.

15. A wearable sensor device comprising:
a transceiver;
a secured storage device;
a power source;
one or more sensors;
a processor, the processor configured to perform a method comprising:
receiving physiological data from the one or more sensors on the wearable device;
obtaining location data from the one or more sensors, wherein the location data comprises global positioning system (GPS) location data of the wearable device;
storing the physiological data and the location data onto the secured storage device;
receiving, by the transceiver, a request to access the physiological data;
accessing a security profile for the physiological data, wherein the security profile defines a normal range associated with the user for the physiological data and defines location data compliance for accessing the physiological data;
providing access to a portion the physiological data for a time period based upon a determination that the portion of the physiological data is outside the normal range for the physiological data and based upon a determination that the location data is in compliance with the security profile, wherein providing access to the portion physiological data comprises transmitting, to a requester, the physiological data from the secured storage device, wherein the secured storage device is in the wearable device;
periodically obtaining additional location data from the one or more sensors during the time period, wherein the additional location data comprises additional GPS location data for the wearable device; and
invoking a security measure for access to the physiological data based upon a determination that the additional location data obtained during the time period is not in compliance with the security profile.

16. The wearable sensor device of claim 15, wherein providing access to the secured data comprises:
displaying, on the wearable device, indicia showing the request to access the physiological data; and
receiving an input, from a user, to allow access to the physiological data.

17. A computer program product for sharing data, the computer program product comprising:
a tangible storage medium readable by a processing circuit and storing instructions for execution by the processing circuit for performing a method comprising:
receiving physiological data from one or more sensors on a wearable device;
obtaining location data from the one or more location sensors, wherein the location data comprises global positioning system (GPS) location data of the wearable device;
storing the physiological data and the location data onto a secured storage device;
receiving, by a transceiver, a request to access the physiological data;
accessing a security profile for the physiological data, wherein the security profile defines a normal range associated with the user for the physiological data and defines location data compliance for accessing the physiological data;
providing access to a portion the physiological data for a time period based upon a determination that the portion of the physiological data is outside the normal range for the physiological data and based upon a determination that the location data is in compliance with the security profile, wherein providing access to the portion physiological data comprises transmitting, to a requester, the physiological data from the secured storage device, wherein the secured storage device is in the wearable device;
periodically obtaining additional location data from the one or more sensors during the time period, wherein the additional location data comprises additional GPS location data for the wearable device; and
invoking a security measure for access to the physiological data based upon a determination that the additional location data obtained during the time period is not in compliance with the security profile.

18. The computer program product of claim 17, wherein providing access to the physiological data comprises:
granting access, to a requester, to the physiological data on the secured storage device, wherein the secured storage device is contained within a cloud computer environment.

* * * * *